United States Patent
Kahn

(10) Patent No.: US 6,982,337 B1
(45) Date of Patent: Jan. 3, 2006

(54) PROCESS FOR MAKING N-VINYL-2-PYRROLIDONE

(75) Inventor: Andrew P. Kahn, Eagleville, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/900,963

(22) Filed: Jul. 28, 2004

(51) Int. Cl.
C07D 207/267 (2006.01)
A61K 31/4015 (2006.01)

(52) U.S. Cl. .................................... 548/408
(58) Field of Classification Search ................ 548/408
See application file for complete search history.

(56) References Cited

U.S. PATENT DOCUMENTS

| | | | |
|---|---|---|---|
| 2,669,570 A | 2/1954 | Schnizer | 260/326.5 |
| 3,821,245 A | 6/1974 | Kanetaka et al. | 260/326.5 |
| 5,410,070 A | 4/1995 | Franz et al. | 548/552 |
| 5,569,770 A * | 10/1996 | Kuo et al. | 548/543 |
| 5,625,076 A | 4/1997 | Shimasaki et al. | 548/552 |
| 5,801,252 A | 9/1998 | Yano et al. | 548/554 |
| 5,994,562 A | 11/1999 | Ebel et al. | 548/543 |
| 6,489,515 B2 | 12/2002 | Kambe et al. | 568/687 |

* cited by examiner

*Primary Examiner*—Kamal A. Saeed
*Assistant Examiner*—Susannah Lee
(74) *Attorney, Agent, or Firm*—Jonathan L. Schuchardt

(57) ABSTRACT

A process for making N-vinyl-2-pyrrolidone (NVP) is disclosed. The process comprises dehydrating N-(2-hydroxyethyl)-2-pyrrolidone (HEP) in the presence of a catalyst and added water. Adding an effective amount of water into the dehydration process reduces the amount of N-ethyl-2-pyrrolidone (NEP) formed compared with the amount produced in the absence of the added water. Adding water can also sustain high conversions of HEP, minimize heavies formation, and improve selectivity to NVP. The process provides high-purity NVP and avoids a costly crystallization step.

9 Claims, No Drawings

PROCESS FOR MAKING N-VINYL-2-PYRROLIDONE

FIELD OF THE INVENTION

The invention relates to a process for making N-vinyl-2-pyrrolidone from N-(2-hydroxyethyl)-2-pyrrolidone. The process provides good yields of NVP while minimizing unwanted by-products.

BACKGROUND OF THE INVENTION

N-vinyl-2-pyrrolidone (NVP) is a monomer used for making crosslinked or uncrosslinked polyvinylpyrrolidones, vinyl pyrrolidone-vinyl ester copolymers, and other valuable polymers. The polymers are used in beverage clarification, hair care, pharmaceutical tablet binding, and other industrial applications.

NVP is commonly manufactured by reacting 2-pyrrolidone with acetylene, but non-acetylenic routes to NVP are available. In one approach, NVP is made by dehydrating N-(2-hydroxyethyl)-2-pyrrolidone (HEP), which is easily obtained by reacting gamma-butyrolactone with 2-aminoethanol.

The dehydrations are normally performed by passing a vaporized mixture of HEP and a diluent gas, usually nitrogen, through a heated reactor tube containing a catalyst. NVP is collected along with water, unreacted HEP, and by-products. The by-products usually include 2-pyrrolidone ("2-Py," a hydrolysis product), N-ethyl-2-pyrrolidone (NEP), and nonvolatile materials ("heavies"). NEP is particularly undesirable because unlike 2-Py, it is not easily converted back to NVP. Moreover, pharmaceutical-grade NVP must be substantially free of NEP, and because NEP and NVP have similar boiling points, an expensive crystallization step is usually needed to separate them. NEP is seldom mentioned in the literature. However, there is at least one report of NEP being observed in an HEP dehydration process catalyzed by alumina (see U.S. Pat. No. 3,821,245 at column 4, line 17).

As noted above, an inert gas such as nitrogen or argon is commonly used to dilute the HEP in the dehydration process. U.S. Pat. No. 5,410,070 teaches (column 2, lines 6–10) that "inert gases, such as hydrogen, nitrogen, or steam, or the addition of inert organic solvents, or the use of reduced pressure can be advantageous." The reference does not say what advantage is expected from using the inert gases, and Table 1 (columns 3–4) shows no examples in which the HEP is combined with nitrogen, steam, or any other diluent.

Despite the availability of a well-known non-acetylenic route to NVP from HEP, the industry would benefit from a process that delivers and sustains higher HEP conversion, better NVP selectivity, reduced NEP formation, and a lower level of non-volatile by-products. An ideal process would be easy to perform using conventional equipment and would use cheap, readily available starting materials.

SUMMARY OF THE INVENTION

The invention is process for making N-vinyl-2-pyrrolidone (NVP). The process comprises dehydrating N-(2-hydroxyethyl)-2-pyrrolidone (HEP) in the presence of a catalyst and added water. I surprisingly found that adding an effective amount of water into the dehydration process reduces the amount of N-ethyl-2-pyrrolidone (NEP) produced compared with the amount of NEP produced in the absence of the added water. Adding the right amount of water can also sustain high conversions of HEP, minimize heavies formation, and improve selectivity to NVP. The process provides high-purity NVP and avoids a costly crystallization step.

DETAILED DESCRIPTION OF THE INVENTION

N-(2-hydroxyethyl)-2-pyrrolidone (HEP) is commercially available. It can also be made by well-known processes, particularly the reaction of gamma-butyrolactone and 2-aminoethanol (ethanolamine). See, e.g., U.S. Pat. Nos. 2,669,570 and 5,801,252, the teachings of which are incorporated herein by reference. The source of the HEP is not critical; any reasonably pure HEP can be used as a starting material for the process of the invention.

Any suitable catalyst can be used for the dehydration step. A variety of useful catalysts have been identified, including oxides of zirconium, aluminum, chromium, cerium, thorium, or zinc (U.S. Pat. No. 3,821,245), mixed Group 4 oxides or Group 4 oxides modified with a metal from Groups 1 or 2 (U.S. Pat. No. 5,569,770), zeolites or other molecular sieves (U.S. Pat. No. 5,994,562), Group 1 or 2 metal-modified silicas or aluminas (U.S. Pat. Nos. 6,489,515, 5,801,252, and 5,625,076), and silicas impregnated with phosphoric acid or a phosphate salt (U.S. Pat. No. 5,410,070). The above-listed patents describe these and other suitable dehydration catalysts and how to make them; their teachings are incorporated herein by reference. Particularly preferred catalysts are silicas, aluminas, silica-aluminas, or titanias that have been modified by treatment with a Group 1 or Group 2 metal. Cesium on silica is especially preferred.

The process of the invention requires that the dehydration process be performed in the presence of an effective amount of added water. By "added water," we mean water that is intentionally introduced into the reaction mixture apart from the water produced in the dehydration reaction. Water can be fed to the reactor in any desired manner. It is conveniently mixed with the HEP feed, but separate feeds of HEP and water can also be used.

In one process of the invention, the water is added in an amount effective to reduce the amount of N-ethyl-2-pyrrolidone (NEP) produced compared with the amount of NEP produced in the absence of the added water. Preferably, the water is added in an amount within the range of 0.5 to 20 wt. %, more preferably from 2 to 10 wt. %, based on the amount of HEP. Preferably, the amount of NEP produced is reduced by at least 50%, more preferably by at least 90%, compared with the amount of NEP produced in the absence of the added water.

Adding an effective amount of water unexpectedly reduces NEP selectivity. The effect becomes more pronounced with prolonged catalyst use. In one example (see Table 2 below), NEP selectivity after 45 hours on stream was reduced from 9.3% to 0.14%. As noted earlier, the ability to minimize or eliminate NEP is particularly valuable for making pharmaceutical-grade NVP.

In another process of the invention, the water is added in an amount effective to enhance conversion of HEP compared with the amount of HEP conversion observed in the absence of the added water. Preferably, the water is added in an amount within the range of 0.5 to 20 wt. %, more preferably from 2 to 10 wt. %, based on the amount of HEP. When less water is added, there is little effect on conversion; larger amounts of water inhibit conversion (see Comparative Example 5, below). Preferably, the HEP conversion is greater than 90%, more preferably greater than 95%, when water is added.

I surprisingly found that adding an effective amount of water enhances HEP conversion. In particular, the ability of the catalyst to promote dehydration for a prolonged time period dramatically improves by adding some water to the HEP. As Example 1 and Comparative Example 2 (Table 1) show, HEP conversion dips to about 7% with an untreated cesium on silica dehydration catalyst after 50 hours of reaction time but is sustained at 92% simply by adding 10 wt. % water to the HEP feed.

Adding an effective amount of water into the HEP dehydration process also reduces the amount of nonvolatile by-products generated. As shown in Tables 1 and 2, the "% heavies" drops modestly (Table 2) or dramatically (Table 1) after many hours on stream when 5–10 wt. % water is included in the HEP feed.

In a preferred process of the invention, the water is added in an amount effective to improve the NVP selectivity. The impact after 45–50 hours on stream is moderate (Table 2) to dramatic (Table 1). In one example, NVP selectivity after 50 h was 90.5% with 10 wt. % added water and compared with 16.3% with no water added.

The % yield of NVP is also enhanced by adding water in an effective amount. Preferably, the NVP yield exceeds 70%, and more preferably it exceeds 80%.

As illustrated below, the dehydrations are conveniently performed by passing a vaporized mixture of HEP and added water through a heated reactor tube that contains the catalyst. A diluent gas such as nitrogen or argon is preferably used to help control the flow of reactants. The reactant mixture is preferably preheated prior to its introduction into the reactor; this helps to stabilize the reactor temperature. The flow rate is adjusted to maintain both a high conversion of HEP and good NVP productivity. The reactor temperature is preferably within the range of 100° C. to 600° C., more preferably from 300° C. to 400° C., and most preferably from 320° C. to 380° C.

Product collection involves simple condensation, which can be accomplished by any desired means. The process of the invention can be monitored conveniently by gas chromatography (GC) analysis to control quality. Distillation, crystallization, or other techniques can be used to further purify the NVP produced. Because the process provides NVP having reduced levels of NEP, a routine distillation will normally be adequate to give NVP with a high purity level, as is needed for pharmaceutical applications. Thus, a more costly purification step can be avoided.

The following examples merely illustrate the invention. Those skilled in the art will recognize many variations that are within the spirit of the invention and scope of the claims.

General

The reactor is a 1" outside diameter (OD), 0.81" inside diameter (ID), 316 stainless steel (SS) tube with a thermowell constructed of 3/16" OD SS running along the centerline of the reactor. The entrance region above the catalyst bed is packed with glass beads to facilitate vaporization of the feed. The reactor effluent is condensed in a cold trap for analysis by gas chromatography (GC). Any mass not accounted for in the GC data is assumed to be nonvolatile material ("heavies").

EXAMPLE 1

The reactor is charged with a 0.44 wt. % cesium on silica catalyst (3.7 g, 14/30 mesh). The reactor is heated to 375° C. A mixture of N-(2-hydroxyethyl)-2-pyrrolidone and water (90 wt. % HEP, fed at 10 g/h) and nitrogen (18 standard L/h) are fed to the reactor, and samples are collected and analyzed. Results appear in Table 1.

COMPARATIVE EXAMPLE 2

Example 1 is repeated, except that water is omitted from the HEP feed. See Table 1.

TABLE 1

Dehydration of HEP to NVP using 10 wt. % Added Water

|  | Example | |
| --- | --- | --- |
|  | 1 | C2 |
| Wt. % water in HEP | 10 | 0 |
| After 3 h on stream: | | |
| % HEP conversion | 97.6 | 98.8 |
| % NVP selectivity | 87.2 | 88.6 |
| % NEP selectivity | 0.05 | 0.09 |
| % 2-Py selectivity | 10.1 | 8.6 |
| % Heavies | 1.8 | 2.6 |
| After 50 h on stream: | | |
| % HEP conversion | 92.0 | 7.4 |
| % NVP selectivity | 90.5 | 16.3 |
| % NEP selectivity | 0.14 | 4.4 |
| % 2-Py selectivity | 5.7 | 4.2 |
| % Heavies | 3.6 | 74.8 |

These examples illustrate that adding 10 wt. % water to the HEP stabilizes HEP conversion, minimizes heavies formation, and controls NEP selectivity while maintaining low selectivity to 2-Py.

EXAMPLE 3

The procedure of Example 1 is followed except that the catalyst is 0.37 wt. % cesium on silica, and the HEP/water mixture contains 95 wt. % HEP. Results appear in Table 2.

COMPARATIVE EXAMPLE 4

The procedure of Example 3 is followed except that water is omitted from the HEP feed. See Table 2.

TABLE 2

Dehydration of HEP to NVP using 5 wt. % Added Water

|  | Example | |
| --- | --- | --- |
|  | 3 | C4 |
| Wt. % water in HEP | 5 | 0 |
| After 3 h on stream: | | |
| % HEP conversion | 96.7 | 99.0 |
| % NVP selectivity | 86.8 | 86.0 |
| % NEP selectivity | 0.05 | 0.06 |
| % 2-Py selectivity | 8.9 | 11.1 |
| % Heavies | 4.2 | 2.8 |

TABLE 2-continued

Dehydration of HEP to NVP
using 5 wt. % Added Water

| | Example | |
|---|---|---|
| | 3 | C4 |
| After 45 h on stream: | | |
| % HEP conversion | 97.4 | 56.7 |
| % NVP selectivity | 90.0 | 71.0 |
| % NEP selectivity | 0.14 | 9.3 |
| % 2-Py selectivity | 6.7 | 5.2 |
| % Heavies | 3.1 | 13.7 |

These examples illustrate that adding 5 wt. % water to the HEP stabilizes HEP conversion, minimizes heavies formation, and controls NEP selectivity while maintaining low selectivity to 2-Py.

COMPARATIVE EXAMPLE 5

The reactor is charged with a 1.6 wt. % cesium on silica catalyst (2.3 g, 14/30 mesh). The reactor is heated to 350° C. A mixture of N-(2-hydroxyethyl)-2-pyrrolidone and water (70 wt. % HEP, fed at 11 g/h) and 10 nitrogen (18 standard L/h) are fed to the reactor, and samples are collected and analyzed. Results appear in Table 3.

COMPARATIVE EXAMPLE 6

The procedure of Comparative Example 5 is followed except that water is omitted from the HEP feed. See Table 3.

TABLE 3

Dehydration of HEP to NVP
using 30 wt. % Added Water

| | Example | |
|---|---|---|
| | C5 | C6 |
| Wt. % water in HEP | 30 | 0 |
| After 24 h on stream: | | |
| % HEP conversion | 51.8 | 89.2 |
| % NVP selectivity | 95.0 | 95.4 |
| % NEP selectivity | 0.04 | 0.04 |
| % 2-Py selectivity | 4.7 | 3.4 |
| % Heavies | 0.3 | 1.2 |

TABLE 3-continued

Dehydration of HEP to NVP
using 30 wt. % Added Water

| | Example | |
|---|---|---|
| | C5 | C6 |
| After 95 h on stream: | | |
| % HEP conversion | 45.7 | 82.5 |
| % NVP selectivity | 93.9 | 91.5 |
| % NEP selectivity | 0.05 | 0.23 |
| % 2-Py selectivity | 4.3 | 3.9 |
| % Heavies | 1.7 | 4.4 |

These examples illustrate that adding 30 wt. % water to the HEP significantly inhibits HEP conversion.

The preceding examples are meant only as illustrations. The following claims define the invention.

I claim:

1. A process which comprises dehydrating N-(2-hydroxyethyl)-2-pyrrolidone (HEP) in the presence of a catalyst and added water to produce N-vinyl-2-pyrrolidone (NVP), wherein the water is used in an amount effective to reduce the amount of N-ethyl-2-pyrrolidone (NEP) produced compared with the amount of NEP produced in the absence of the added water.

2. The process of claim 1 wherein conversion of HEP is enhanced by adding the water.

3. The process of claim 1 wherein selectivity to NVP is enhanced by adding the water.

4. The process of claim 1 wherein production of nonvolatile by-products is reduced by adding the water.

5. The process of claim 1 wherein the water is added in an amount within the range of 0.5 to 20 wt. % based on the amount of HEP.

6. The process of claim 1 wherein the water is added in an amount within the range of 2 to 10 wt. % based on the amount of HEP.

7. The process of claim 1 wherein the catalyst is cesium on silica.

8. The process of claim 1 wherein the yield of NVP exceeds 80%.

9. The process of claim 1 wherein the amount of NEP produced is reduced by at least 50% compared with the amount of NEP produced in the absence of the added water.

* * * * *